(12) United States Patent
Carpenter et al.

(10) Patent No.: US 8,372,798 B2
(45) Date of Patent: Feb. 12, 2013

(54) HIGH-CONCENTRATION PROTEIN FORMULATIONS AND METHOD OF MANUFACTURE

(75) Inventors: John F. Carpenter, Littleton, CO (US); Jeffrey B. Etter, Boulder, CO (US); Adrian C. Samaniego, Louisville, CO (US)

(73) Assignee: Endo Pharmaceuticals Colorado, Inc., Chadds Ford, PA (US)

( * ) Notice: Subject to any disclaimer, the term of this patent is extended or adjusted under 35 U.S.C. 154(b) by 2288 days.

(21) Appl. No.: 10/271,832

(22) Filed: Oct. 16, 2002

(65) Prior Publication Data

US 2003/0092607 A1 May 15, 2003

Related U.S. Application Data

(60) Provisional application No. 60/330,213, filed on Oct. 16, 2001.

(51) Int. Cl.
*A61K 49/14* (2006.01)

(52) U.S. Cl. ........ 514/1.1; 514/21.2; 514/21.3; 530/350; 530/386

(58) Field of Classification Search .................. 424/400
See application file for complete search history.

(56) References Cited

U.S. PATENT DOCUMENTS

| | | | |
|---|---|---|---|
| 4,276,283 A * | 6/1981 | Eibl et al. ............... | 424/177.1 |
| 5,488,034 A | 1/1996 | McGregor et al. ........ | 514/12 |
| 5,702,717 A | 12/1997 | Cha et al. ............... | 424/425 |
| 5,707,648 A | 1/1998 | Yiv ....................... | 424/450 |
| 5,861,158 A * | 1/1999 | Kwak et al. ............. | 424/184.1 |
| 5,861,174 A | 1/1999 | Stratton et al. .......... | 424/484 |
| 6,228,360 B1 * | 5/2001 | Co et al. ................ | 424/145.1 |
| 6,267,958 B1 | 7/2001 | Andya et al. ............ | 424/130.1 |
| 6,875,441 B2 * | 4/2005 | Rosenthal et al. ........ | 424/422 |
| 2005/0019325 A1 * | 1/2005 | Carter et al. ............ | 424/144.1 |
| 2005/0038254 A1 * | 2/2005 | Michels et al. .......... | 546/217 |

OTHER PUBLICATIONS

L.A. Garcia and G.A. Ordonez, et al., The Use of Pluronic Polyols in the Precipitation of Plasma Proteins and Its Application in the Preparation of Plasma Derivatives, Transfusion, 1976, vol. 16, pp. 32-41.*

Stratton et al. "Drug delivery matrix containing native protein precipitates suspended in a poloxamer gel," J. Pharm Sci., 1997, 86, 1006-10.*

Jeong et al., "Biodegradable block copolymers as injectable drug-delivery systems," Nature, 1997, 388, 860.*

Johnston et al. "Sustained delivery of interleukin-2 from a poloxamer 407 gel matrix following intraperitoneal injection in mice," Pharm. Res., 1992, 9, 425.*

Wang & Johnston, "Sustained-release interleukin-2 following intramuscular injection in rats," Int. J. Pharm., 1995, 113, 73.*

Bhardwaj & Blanchard, "Controlled-release delivery system for the a-MSH analog melanotan-I using poloxamer 407," J. Pharm. Sci., 1996, 85, 915.*

Pec et al. "Biological activity of urease formulated n poloxamer 407 after intraperitoneal injection in the rat," J. Pharm. Sci., 1992, 81, 626.*

Wang et al. 'Sustained-Release Interleukin-2 Following Intramuscular Injection in Rats' Inter. J. of Pharm. vol. 113, pp. 73-81. 1995.*

Garcia, L.A. et al, The Use of Pluronic Polyols in the Precipitation of Plasma Proteins and Its Application in the Preparation of Plasma Derivatives, Transfusion, vol. 16, No. 1, pp. 32-41, Jan.-Feb. 1976.

Mustafa, A.O. et al. A novel approach for the crystallization of soluble proteins using non-ionic surfactants. Acta Crystallographica Section D. vol. 54, Part 1. pp. 154-158. 1998.

Johnston et al. Sustained Delivery of Interleukin-2 From a Poloxamer 407 Gel Matrix Following Intraperitoneal Injection in Mice. Pharmaceutical Research, vol. 9, No. 3, pp. 425-434. 1992.

Dorland's Illustrated Medical Dictionary, Edition 28, W.B. Sanders Company, 1994, definitions of "antibody" and "immunoglobulin", pp. 92-93, 823-825.

* cited by examiner

*Primary Examiner* — Anish Gupta
(74) *Attorney, Agent, or Firm* — Marsh Fischmann & Breyfogle LLP

(57) ABSTRACT

Provided is a pharmaceutical composition involving a concentrated mixture of a precipitated protein and a liquid medium and a method for manufacturing the concentrated mixture. The concentrated mixture is manufacturable by precipitation of a protein with a biocompatible polymer precipitating agent, followed by removal of sufficient liquid to concentrate the resulting mixture to the desired degree. The precipitated protein can be stored for a significant time in the concentrated mixture, such as intermediate between processing stages during manufacture operations.

56 Claims, 5 Drawing Sheets

HIGH-CONCENTRATION PROTEIN FORMULATIONS AND METHOD OF MANUFACTURE

CROSS-REFERENCE TO RELATED APPLICATIONS

This application claims a priority benefit under 35 U.S.C. §119(e) to prior U.S. Provisional Patent Application No. 60/330,213, entitled "HIGH-CONCENTRATION PROTEIN FORMULATIONS AND METHOD OF MANUFACTURE," filed Oct. 16, 2001, the entire contents of which are incorporated herein as if set forth herein in full.

BACKGROUND OF THE INVENTION

Therapeutic treatment with some proteins, and particularly immunoglobulins, requires administration of a large dose. Due to their unique ability to recognize and bind to specific targets, immunoglobulins in particular hold great promise for therapeutic treatments in the fights against diseases such as cancer and arthritis. Some drawbacks to treatment with immunoglobulins, however, include low potency on a mass basis due to a typically large molecular weight, a relatively low solubility in water and requirements for effective long-term storage. For example, typical monoclonal IgG antibodies have molecular weights of approximately 150 kDa, have an aqueous solubility limit of less than 50 mg/mL and must be lyophilized for long-term storage.

Also, due to the noted low potency on a mass basis, commercially available therapeutic antibodies have dosing regiments that usually require administration of between 100 mg and 1000 mg per dose. Low solubility in water means that several milliliters of antibody solution must be administered for administration of a single dose. Even assuming solubility as high as 50 mg/mL for the antibody, a 100 mg dose would require administration of 2 mL of solution, while a 1000 mg dose would require administration of 20 mL of solution. These volumes are too large for administration applications such as subcutaneous (SC), intramuscular (IM), intratumoral (IT) and intraarticular (IA) injections, which are generally limited to a 1 mL volume. It has, therefore, been necessary to administer these therapeutic agents as IV infusions. Such IV infusions are time consuming and inconvenient for medical staff and patients.

An additional limitation imposed by the relatively low solubility of antibody proteins is related to their production. After large-scale fermentation it is often desirable to hold material at an intermediate stage in order to combine several batches to create a large lot of product. The volume of the intermediate material must be sufficiently small to be conveniently stored at the manufacturing facility. Diafiltration of dilute solutions can lead to precipitation and membrane fouling. Large-scale freeze-drying requires significant investments in space, capital equipment and operating costs.

Attempts have been made to prepare highly concentrated antibody solutions by careful control of pH, ionic strength and buffer type, but many antibodies and other proteins cannot be dissolved at high concentrations even under the best of conditions. Also, even when it is possible to dissolve the antibody to a high concentration, it is still very difficult to maintain adequate protein stability in such high concentration solutions during long-term storage. In particular, the risk of formation of highly undesirable non-native aggregates increases as the concentration of the protein in the solution increases. Furthermore, the high viscosity exhibited by some high-concentration antibody solutions often complicates, and in some cases precludes, practical processing of the materials during manufacturing operations.

For reasons of product stability, therapeutic antibodies are currently supplied to clinical practices in lyophilized form. Freeze-dried vials are stored under refrigerated conditions and must be reconstituted prior to use. The reconstitution procedure is time consuming because lyophilized cake does not quickly reconstitute. Also, the reconstitution can result in degradation of the therapeutic protein through foaming and denaturation. The reconstitution process can therefore, lead to variability in both the administration dose and relative activity/immunogenicity of the therapeutic agent.

There is a significant need for improved high-concentration protein formulations, and there is especially a need for antibody formulations suitable for administration by applications such as SC, IM, IT and IA injection. There is also a significant need for improved techniques for processing and storing intermediate products during manufacture of antibody and other protein products. There is a further need for techniques for long-term storage of antibodies and other proteins that reduce or eliminate problems with reconstitution of lyophilized products.

SUMMARY OF THE INVENTION

With the present invention, it has been found that stable concentrated protein formulations can be prepared without requiring lyophilization. The concentrated protein formulation is a mixture of the protein in precipitated form and a liquid medium, typically an aqueous medium. It has been found that the precipitated protein in the concentrated mixture is highly stable, advantageously permitting storage for an extended time without the expense and complexity involved with lyophilization. Also, the concentrated mixture is readily dilutable to reconstitute the precipitated protein in a more dilute formulation, as may be desired for further processing or for administration. During manufacture of the concentrated mixture and/or during subsequent dilution to prepare a more dilute formulation, additives, such as protein stabilizers and surfactants, can be added to impart desired characteristics to the pharmaceutical composition.

The present invention is particularly useful with macromolecular proteins, and especially antibodies, which are often difficult to formulate in sufficiently concentrated and injectable formulations for administration by routes such as IM, SC, IT or IA injection. With the present invention, concentrated yet injectable suspensions of proteins, and especially antibodies, can be prepared that are suitable for administration by routes such as IM, SC, IT and IA injection.

In one aspect, the present invention provides a method for preparing pharmaceutical compositions including a protein. The pharmaceutical composition could be a final composition designed for administration, or could be an intermediate composition that is designed for extended storage awaiting further processing or dilution to prepare a final composition for administration. In a particularly advantageous application, the method involves precipitation of a protein of interest from a solution in which the protein is dissolved by contacting the solution with a suitable precipitating agent; followed by removal of sufficient liquid from the resulting mixture to prepare a concentrated mixture comprising at least 8 weight percent of the precipitated protein, and preferably at least 10 weight percent of the precipitated protein. Also, for enhanced storage and reconstitution of the precipitated protein, the concentrated mixture should preferably include at least 20 weight percent water, and more preferably at least 30 weight percent water. This is in sharp contrast to lyophilized cakes that typically include significantly less than 10 weight percent water and can be very difficult to reconstitute for administration.

In a particularly preferred embodiment of this aspect of the invention, the precipitating agent is a biocompatible polymer, and preferably a reverse-thermal gelation polymer. The biocompatible polymer not only causes precipitation of the protein, but the presence of the biocompatible polymer in the concentrated mixture provides additional protection to stabilize the protein during storage for an extended time.

In one application of the method, the concentrated mixture is designed for extended storage of the protein of interest in a stable form. In this situation, the concentrated mixture will typically comprise at least 40 weight percent of the precipitated protein, and preferably an even higher concentration of the protein.

In one enhancement, a protein stabilizer, such as sucrose, trehalose or mannitol, is added during the method to further enhance stability of the precipitated protein in the concentrated mixture for extended storage. Also, polyols and/or surfactants, such as mannitol or a polysorbate, can advantageously be included in the concentrated mixture to enhance injectability of a final pharmaceutical composition.

In one aspect, the invention provides a method for preparing a pharmaceutical composition, typically in a final formulation designed for administration. The method involves diluting a concentrated mixture of the precipitated protein to prepare a more dilute mixture of the precipitated protein. Typically the dilution will be performed in a manner to prevent any substantial portion of the protein from dissolving into the liquid medium of the diluted mixture. By maintaining the amount of dissolved protein to a small or insignificant amount, the potential for formation of undesirable non-native aggregates is significantly reduced, which is beneficial to long-term stability of the formulation.

In another aspect, the invention provides a method for storage of a protein for an extended time, typically for at least one month and often for 3 months or more. The protein is stored in a concentrated mixture of the protein in precipitated form. To further enhance stability during storage, the concentrated mixture can be frozen. In another embodiment, the concentrated mixture can be converted to a gel form when the concentrated mixture includes a sufficient concentration of a biocompatible reverse-thermal gelation polymer.

In another aspect, the invention provides a method for packaging a protein. The method involves placing a quantity of a concentrated mixture of a precipitated protein in a sealed container. In one preferred embodiment, the contained quantity includes a single dose of the protein for administration, and more preferably the contained quantity has a volume of no larger than 1 mL.

In another aspect, the invention provides a pharmaceutical composition comprising a concentrated mixture of a precipitated protein. In a preferred embodiment, the composition includes a high concentration of the protein, and also a significant quantity of water to facilitate ready reconstitution of the precipitated protein into a more dilute formulation. In one embodiment, the composition is designed as a final composition for administration, and is preferably sufficiently injectable for administration of the composition by a technique such as IM, SC, IT or IA injection. In one embodiment, the pharmaceutical composition is packaged so that the pharmaceutical composition includes a single dose of the precipitated protein contained in a sealed container, such as a vial or bottle. In the case of administration by routes such as IM, SC, IT or IA injection, the contained quantity of the pharmaceutical composition is preferably no larger than 1 mL. In another embodiment, the pharmaceutical composition is contained within an injection device, such as a syringe.

In another aspect, the invention provides a method for administering the pharmaceutical composition by injection to a patient, and preferably by a route such as IM, SC, IT or IA injection. The patient can be a human or animal patient.

Both the foregoing summary and the following detailed description, including the examples, are exemplary and are intended to provide explanation of the invention as claimed. Other aspects and novel features will be readily apparent to those skilled in the art from the following detailed description of the invention.

DETAILED DESCRIPTION

Figure 1:
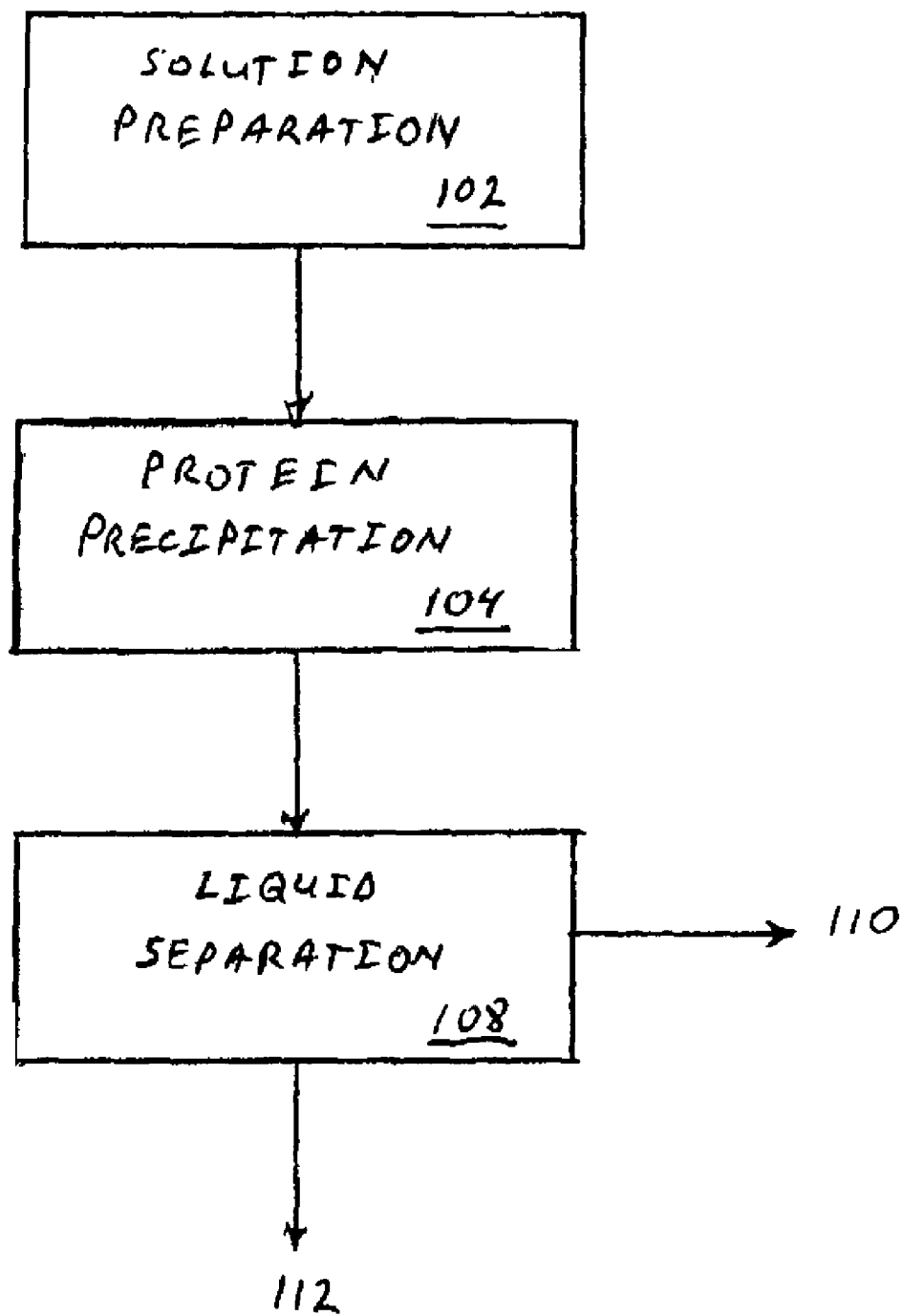
FIG. 1 is a generalized process block diagram showing one embodiment of the method of the present invention to prepare a concentrated mixture containing a high concentration of precipitated protein.

In one aspect, the invention provides a method for preparing a pharmaceutical composition in the form of a concentrated formulation of a protein. Referring to FIG. 1, a generalized process block diagram of one embodiment of the method is shown. As shown in FIG. 1, a first step is solution preparation 102, during which a solution of a protein is made with the protein dissolved in a liquid medium. After the solution preparation 102, the protein is precipitated during protein precipitation 104, during which the protein solution is contacted with a precipitating agent, causing the protein to precipitate out of solution. The protein precipitation 104 results in a mixture including the precipitated protein and liquid medium. After the protein precipitation 104, liquid is separated from the mixture in a liquid separation step 108 to produce a separated liquid 110 and a concentrated mixture 112. The concentrated mixture 112 includes a high concentration of the precipitated protein. By precipitated protein, it is meant the protein in a particulate form as precipitated from solution during the protein precipitation 104. The precipitated protein is fully reversible and contains protein molecules in which the native protein secondary structure has not bee substantially perturbed. This should be contrasted with undesirable irreversible aggregates that fall out of solution and contain protein molecules with substantially non-native secondary structure.

The solution preparation 102 can be accomplished in any manner to dissolve the protein in a suitable liquid medium. The liquid medium will typically be an aqueous liquid of suitable salinity, pH and ionic strength to dissolve the protein at issue to the desired concentration. The concentration of the protein in the solution will vary depending upon the particular protein being processed. It is not, however, necessary that the protein be highly concentrated in the solution. Rather, it is generally preferred that the concentration of the protein in the solution is relatively low, for ease of preparation and handling of the solution during processing. Such relatively low concentration protein solutions are frequently prepared during manufacture operations. In most situations, the concentration of the protein in the solution is no larger than 50 mg/mL, more typically no larger than 25 mg/mL and even more typically no larger than 10 mg/mL. Very low concentrations are particularly preferred for extremely large proteins, such as antibodies.

The protein used with the method of the present invention can be any protein for which a highly concentrated formulation is desired. Proteins typically have molecular weights of 15 kD or higher. Preferred for use with the present inventions are the higher molecular weight proteins, those having a molecular weight of at least 100 kD, for which it is often difficult or not possible to prepare at high concentrations in solution. These higher molecular weight proteins are referred to herein as macromolecular proteins. The lower molecular weight proteins, however, can also be advantageously processed with the present invention. Even lower molecular weight proteins that can be dissolved at high concentrations in aqueous media benefit from being in the more stable precipitate state with the present invention. This enhanced formulation stability is particularly useful for extended storage of proteins, such as may occur between certain processing operations during manufacture. Some specific examples of proteins for use with the present invention are listed in U.S. Pat. No. 6,267,958, the entire contents of which is incorporated herein as if set forth herein in full. Some preferred proteins for use with the present invention include growth factors, soluble receptors, cytokines, hemophilia factors and antibodies.

Antibodies, which typically have a molecular weight of about 150 k Daltons or more, are particularly preferred as proteins for use with the present invention. Any antibody can be used with the present invention. U.S. Pat. No. 6,267,958 discusses some specific antibodies for use with the present invention. For example, the antibody could be or include a monoclonal antibody, a composition having polyepitopic specificity, a bispecific antibody, a diabody, a single-chain molecule, and an antibody fragment.

In a preferred embodiment, the protein should typically be essentially pure, in that is it should be substantially in the absence of contaminating proteins. Preferably the protein is at least 90 weight percent pure, more preferably at least 95 weight percent pure and even more preferably at least 99 weight percent pure prior to the solution preparation 102.

Furthermore, the protein is typically not purified during the solution preparation 102, protein precipitation 104 or liquid separation 108 steps. It is preferred that the method effects substantially only a concentration of the protein in precipitated form and does not purify the protein. In a preferred embodiment, the purity of the protein in the precipitation is essentially the same as in the protein solution from which the protein is precipitated during the protein precipitation 104.

The precipitating agent contacted with the protein solution during the protein precipitation 104 can be any material in a form capable of causing precipitation of at least a portion of the protein, and preferably most or substantially all of the protein. Typically at least 80 weight percent, preferably at least 90 weight percent, even more preferably at least 95 weight percent, still more preferably at least 98 weight percent, and most preferably at least 99 weight percent of the protein is precipitated during the protein precipitation 104. Correspondingly, preferably little protein remains dissolved in the liquid medium following the precipitation 104. Typically, no more than 20 weight percent, preferably no more than 10 weight percent, even more preferably no more than 5 weight percent, even more preferably no more than 2 weight percent and most preferably no more than 1 weight percent of the protein remains dissolved in the liquid medium following the precipitation 104. Precipitation of as much of the protein as possible is important to enhance stability in the concentrated mixture 112, facilitating long-term storage.

For enhanced performance, the precipitating agent should be biocompatible, because at least a portion of the precipitating agent will remain in the concentrated mixture 112, and it is contemplated that in most, if not all, situations at least a portion of the precipitating agent will remain with the precipitated protein during administration of the precipitated protein to a patient. By biocompatible, it is meant that a substance does not have toxic or injurious effects on biological function in a host.

Preferred for use as the precipitating agent is a biocompatible polymer or mixture of biocompatible polymers that, when contacted with the protein solution during the protein precipitation 104, results in the desired precipitation of the protein from solution. The biocompatible polymer may be any biocompatible polymer capable of being contacted with the protein solution to effect the desired precipitation of the protein. The biocompatible polymer will typically be dissolved in a solution, typically an aqueous solution, prepared separately from the protein solution. The polymer solution and the protein solution are then mixed during the protein precipitation 104, either by adding the polymer solution to the protein solution or by adding the protein solution to the polymer solution, with the latter being preferred.

One preferred biocompatible polymer for use with the present invention as the precipitating agent is a reverse-thermal gelation polymer. In one embodiment, the biocompatible polymer is selected and the polymer and protein solutions are formulated so that the biocompatible polymer in the resulting mixture, and also in the concentrated mixture 112, is present at a concentration so that at least the liquid portion of the respective mixture exhibits reverse-thermal viscosity behavior across at least some temperature range, preferably a temperature range below 40° C., more preferably a temperature range below 37° C. and even more preferably a temperature range within a range of from 10° C. to 37° C. Typically, the liquid exhibits reverse-thermal viscosity behavior over some temperature range within a range of 1° C. to 20° C. Due to the reverse-thermal viscosity behavior of the liquid in the concentrated mixture 112, the concentrated mixture 112 can be administered to a host at a cooler temperature where the composition has a lower viscosity. When the liquid of the concentrated mixture 112 has a reverse thermal gelation property, then the liquid of the concentrated mixture 112 will be in the form of a flowable medium at least at a first temperature and in the form of a gel at least at a second temperature that is higher than the first temperature. Preferably both the first and second temperatures are below 40° C., and more preferably the second temperature is no higher than 37° C. A preferred situation is when the first temperature is in a range of 1° C. to 20° C. and the second temperature is in a range of 25° C. to 37° C.

In one embodiment, the liquid in the mixture following the protein precipitation and the liquid in the concentrated mixture 112 each contain a concentration of the reverse-thermal gelation polymer at a level so that the liquid has a reverse-thermal gelation property, preferably with a reverse-thermal liquid-gel transition temperature so that when the concentrated mixture 112 is administered to a host, the biocompatible polymer converts from a liquid to a gel state in vivo. In another embodiment, the concentration of the reverse-thermal gelation polymer is not large enough to permit formation of the gel form of the polymer during storage, administration or after administration. This latter situation will often be preferred for administration by IM, SC, IT or IA injection.

As used herein, the terms "reverse-thermal viscosity property" and "reverse-thermal viscosity behavior" each refer to a property of a component or components, and in particular a biocompatible polymer/water combination, to undergo a viscosity increase with increasing temperature across at least some temperature range. "Reverse-thermal gelation property" refers to a property of a component or components, and in particular a biocompatible polymer/water combination, to change from a liquid form to a gel form as the temperature is raised from below to above a reverse-thermal liquid-gel transition temperature. "Reverse-thermal liquid-gel transition temperature" refers to a temperature at which, or a temperature range across which, a component or components, and in particular a biocompatible polymer/water combination, changes physical form from a liquid form to a gel form as the temperature of the material is increased. "Reverse-thermal gelation polymer" refers to a polymer capable of interacting with a liquid vehicle, and particularly water, so that the polymer/liquid vehicle combination exhibits a reverse-thermal gelation property at least at some proportions of the polymer and the liquid vehicle.

Non-limiting examples of some biocompatible reverse-thermal gelation polymers include certain polyethers (preferably polyoxyalkylene block copolymers with more preferred polyoxyalkylene block copolymers including polyoxyethylene-polyoxypropylene block copolymers referred to herein as POE-POP block copolymers, such as Pluronic™ F68, Pluronic™ F127, Pluronic™ L121, and Pluronic™ L101, and Tetronic™ T1501); certain cellulosic polymers, such as ethylhydroxyethyl cellulose; and certain poly (ether-ester) block copolymers (such as those disclosed in U.S. Pat. No. 5,702,717, the entire contents of which are incorporated by reference herein as if set forth herein in full). Pluronic™ and Tetronic™ are trademarks of BASF Corporation. Furthermore, more than one of these and/or other biocompatible polymers may be included in the polymer solution. Also, other polymers and/or other additives may also be included in the polymer solution and/or the protein solution to the extent the inclusion is not inconsistent with the conduct of the method of the present invention or the performance requirements of the concentrated mixture 112. Furthermore, these polymers may be mixed with other polymers or other additives, such as sugars, to vary the transition temperature, typically in aqueous solutions, at which reverse-thermal gelation occurs.

Polyoxyalkylene block copolymers are particularly preferred as biocompatible polymers for use as the precipitating agent. A polyoxyalkylene block copolymer is a polymer including at least one block (i.e. polymer segment) of a first polyoxyalkylene and at least one block of a second polyoxyalkylene, although other blocks may be present as well. POE-POP block copolymers are one class of preferred polyoxyalkylene block copolymers for use as the biocompatible reverse-thermal gelation polymer in the formulated biocompatible polymer. POE-POP block copolymers include at least one block of a polyoxyethylene and at least one block of a polyoxypropylene, although other blocks may be present as well. The polyoxyethylene block may generally be represented by the formula $(C_2H_4O)_b$ when b is an integer. The polyoxypropylene block may generally be represented by the formula $(C_3H_6O)_a$ when a is an integer. The polyoxypropylene block could be for example $(CH_2CH_2CH_2O)_a$, or could be

Several POE-POP block copolymers are known to exhibit reverse-thermal gelation properties, and these polymers are particularly preferred for imparting reverse-thermal viscosity and/or reverse-thermal gelation properties to the concentrated mixture 112. Examples of POE-POP block copolymers include Pluronic™ F68, Pluronic™ F127, Pluronic™ L121, Pluronic™ L101, and Tetronic™ T1501. Tetronic™ T1501 is one example of a POE-POP block copolymer having at least one polymer segment in addition to the polyoxyethylene and polyoxypropylene segments. Tetronic™ T1501 is reported by BASF Corporation to be a block copolymer including polymer segments, or blocks, of ethylene oxide, propylene oxide and ethylene diamine.

As will be appreciated, any number of biocompatible polymers may now or hereafter exist that are capable of acting as the precipitating agent, and such polymers are specifically intended to be within the scope of the present invention when incorporated into the formulated biocompatible polymer.

Some preferred POE-POP block copolymers have the formula:

   I which, in the preferred embodiment, has the property of being liquid at ambient or lower temperatures and existing as a semi-solid gel at mammalian body temperatures wherein a and b are integers in the range of 15 to 80 and 50 to 150, respectively. A particularly preferred POE-POP block copolymer for use with the present invention has the following formula:

   II wherein a and b are integers such that the hydrophobe base represented by $(CH_2(CH_3)CHO)_a$ has a molecular weight of about 4,000, as determined by hydroxyl number; the polyoxyethylene chain constituting about 70 percent of the total number of monomeric units in the molecule and where the copolymer has an average molecular weight of about 12,600. Pluronic™ F-127, also known as Poloxamer 407, is such a material. In addition, a structurally similar Pluronic™ F-68 may also be used.

One advantage to the use of a biocompatible polymer relative to the use of nonpolymeric precipitating agents is that the biocompatible polymer helps to protect and stabilize the protein in the concentrated mixture 112. This is especially the case when using a reverse-thermal gelation polymer, such as the preferred polyoxyalkylene polymers. In that regard, when the reverse-thermal gelation polymer is present in a concentration that imparts a reverse-thermal gelation property, the formation of a gel as the temperature is raised further protects the protein from degradation.

Some nonpolymeric precipitating agents, which are not preferred for use with the present invention, include certain zinc salts, ammonium sulfate, sodium acetate and ethanol. These precipitating agents are not preferred, because they are not as benign for administration as the biocompatible polymer.

During the protein precipitation 104, the precipitating agent can be contacted with the protein solution in any way that effects the desired precipitation of the protein. Typically, the precipitating agent will be dissolved in a second solution that is added to the protein solution, or to which the protein solution is added, typically with stirring or some other form of active mixing.

The precipitating agent can be used in any quantity sufficient to effect the desired precipitation during the protein precipitation 104. For example, the biocompatible polymer precipitating agent will typically be prepared in a separate polymer solution comprising the biocompatible polymer at a concentration of typically at least 5 weight percent and typically no larger than 40 weight percent. Preferably, the biocompatible polymer is completely dissolved in the polymer solution prior to the protein precipitation 104. After mixing the polymer solution and the protein solution during the protein precipitation, the concentration of the polymer in the resulting mixture is typically at least 5 weight percent and typically no larger than 30 weight percent. Some of the biocompatible polymer in the mixture resulting from the protein precipitation will remain in solution in the liquid phase, and some of the biocompatible polymer will be in the solid phase along with the precipitated protein. The solid phase resulting from the protein precipitation will typically comprise only a few percent of the total mixture, with the solid content falling in a range of from 1 weight percent to 10 weight percent of the resulting mixture in most situations.

In one enhancement of the method of the invention, one or more additive can be added during processing in addition to the protein and the precipitating agent. One particularly useful additive is a protein stabilizer that helps to further stabilize the protein in the concentrated mixture 112. The protein stabilizer is any molecule that significantly prevents or reduces instability, either chemical or physical, of the protein when incorporated into the concentrated composition 112. Examples of some protein stabilizers useful with the present invention include substances that have traditionally been used to stabilize lyophilized proteins. A number of these so-called lyoprotectants are described in U.S. Pat. No. 6,267,958. Preferred for use as a protein stabilizer with the present invention are sugars. Particularly preferred are the sugars sucrose and trehalose. Another preferred protein stabilizer is mannitol.

When used, the protein stabilizer can be introduced as part of the protein solution, as part of the polymer solution or separate from the protein and polymer solutions. Preferably, the protein stabilizer is added prior to the liquid separation 108, and more preferably the protein stabilizer is codissolved in at least one of the protein solution and the polymer solution.

The addition of the protein stabilizer helps to enhance the stability of the protein in the concentrated mixture 112. The stable nature of the concentrated mixture 112 is particularly advantageous because it is achieved without the complexity and expense of lyophilization.

Another additive that can advantageously be added during manufacture or after manufacture is an additive to improve the flow properties of the concentrated mixture 112, such as to improve injectability. Surfactants and polyols are examples such flow-enhancing additives. The addition of a surfactant and/or a polyol is especially useful for enhancing the syringeability of the concentrated mixture 112, especially when the concentrated mixture 112 is extremely highly concentrated in the protein. Nonionic, biocompatible surfactants and polyols are preferred. Nonlimiting examples of some polyols and/or surfactants can be found in U.S. Pat. No. 6,267,958. Preferred for use as a surfactant with the present invention are polysorbates. Some preferred polyols include mannitol and glycerol. One preferred polysorbate surfactant is distributed under the Tween™ label by Uniqema (ICI Group). Other preferred surfactants include sorbitan esters, such as those distributed under the Span™ label by Uniqema (ICI Group). The enhanced injectability that can sometimes be achieved with the use of a surfactant and/or a polyol is particularly noteworthy and advantageous, especially when it is desired to administer extremely concentrated formulations of the protein by IM, SC, IT or IA injection.

During the liquid separation 108, at least a portion, and typically a majority, of the liquid is removed from the protein precipitate. The separation can be accomplished using any liquid-solid separation technique. Possible separation techniques include settling of the protein precipitate followed by decantation of supernatant liquid, centrifuging, filtration, cycloning, etc. Settling of the protein precipitate followed by decantation of supernatant liquid is preferred because it is relatively easy to maintain an antiseptic environment during such an operation. The separated liquid 110 is typically discarded. The concentrated mixture 112 will advantageously comprise a concentrated formulation of the precipitated protein and the remaining liquid. During the liquid separation 108, sufficient liquid is removed to provide the desired concentration of the precipitated protein in the concentrated mixture 112. The desired concentration of the precipitated protein will vary depending upon the particular protein being processed and the particular situation. One significant advantage of the present invention is that the concentrated mixture 112 can be produced with a wide variety of precipitated protein concentrations, permitting great flexibility in preparing the concentrated mixture 112 at a specific desired concentration of the precipitated protein for any particular application. However, the concentration of the precipitated protein in the concentrated mixture 112 will typically be in a range of from 8 weight percent to 80 weight percent, and more typically in a range of from 10 weight percent to 70 weight percent of the concentrated mixture 112. At the lower end of the exemplary precipitated protein concentration ranges, the concentration of the precipitated protein should be large enough for use for administration by techniques such as IM, SC, IT and IA injection. At the higher end of the exemplary concentration range, it is important to retain at least enough water so that the concentrated mixture 112 could later easily be diluted with additional water to reconstitute the precipitated protein at a lower concentration for administration. The concentrated mixture 112 preferably will include water in a range having a lower limit of typically 10 weight percent, more typically 20 weight percent and even more typically 30 weight percent of the concentrated mixture 112 and an upper limit of typically 92 weight percent and more typically 90 weight percent. If too much water is removed during the liquid separation 108, reconstitution could suffer some of the problems often experienced with reconstitution of lyophilized proteins. By maintaining at least a significant concentration of water in the concentrated mixture 112, the concentrated mixture 112 is easily diluted to reconstitute the precipitated protein into a more dilute mixture suitable for administration or for further processing, as desired. In addition to water and the precipitated protein, the concentrated mixture 112 will also include at least some of the precipitating agent, and may include other additives as well, such as a surfactant, polyol and/or protein-stabilizer. The concentration of the precipitating agent in the concentrated mixture 112 will vary depending upon the specific precipitating agent being used and the conditions of precipitation. When using a biocompatible polymer precipitating agent, the concentrated mixture 112 includes typically at least 5 weight percent of the biocompatible polymer and typically no more than 50 weight percent of the biocompatible polymer, with biocompatible polymer concentrations of from 10 to 30 weight percent being more common. When used, the surfactant will be added during manufacture in an amount of that is typically at least 0.001 weight percent relative to the protein and that is typically no larger than 1 weight percent relative to the protein, and will then generally be present in the concentrated mixture 112 at approximately those same concentrations relative to the precipitated protein. When used, the protein stabilizer will be added during manufacture in an amount that is typically at least 10 weight percent relative to the protein and that is typically no larger than 1000 weight percent relative to the protein, and will then generally be present in the concentrated mixture 112 at approximately those same concentrations relative to the precipitated protein.

If the concentrated mixture 112 is to be used as a final pharmaceutical formulation for administration, then the concentration of the precipitated protein should preferably be high enough to permit a full dose of the protein to be administered by injection in a volume of 1 mL, permitting administration by techniques such as IM, SC, IT and IA injection. In this situation, and especially for antibodies, the concentrated mixture 112 will have a concentration of the precipitated protein that is in a range having a lower limit of typically 8 weight percent, more typically 10 weight percent, and often 20 weight percent of the concentrated mixture 112 and having an upper limit of typically 50 weight percent, more typically 40 weight percent, even more typically 35 weight percent and often 30 weight percent of the concentrated mixture 112. Correspondingly, the concentrated mixture 112 will contain water in an amount in a range having a lower limit of typically 50 weight percent, more typically 60 weight percent, even more typically 65 weight, and often 70 weight percent of the concentrated mixture 112 and having an upper limit of typically 92 weight percent and more typically 90 weight percent of the concentrated mixture 112. A particularly preferred range for the concentration of the precipitated protein for administration by IM, SC, IT and IA injection is from 10 weight percent to 30 weight percent, which permits great flexibility for administration of a number of antibodies. A number of antibodies will require a concentration in a range of 20 weight percent to 30 weight percent of the concentrated mixture 112. It is important in the case of administration, however, that the concentrated mixture be sufficiently injectable to be administered by IM, SC, IT or IA injection, a situation that is often achievable with the present invention.

One particular advantage of the present invention is use of the concentrated mixture 112 as an intermediate product that is easily stored for extended times between processing steps in protein manufacture operations. In this situation, it is generally desired that, during the liquid separation 104, most of the liquid be removed so that the concentrated mixture 112 will be very highly concentrated in the precipitated protein, to greatly reduce the volume that must be handled and stored while awaiting further processing. In this situation, and especially for antibodies, the concentrated mixture 112 will have a concentration of the precipitated protein that is in a range having a lower limit of typically 20 weight percent, more typically 30 weight percent, even more typically 40 weight percent and most typically 50 weight percent of the concentrated mixture 112 and having an upper limit of typically 90 weight percent, more typically 80 weight percent and even more typically 70 weight percent of the concentrated mixture 112. Correspondingly, the concentrated mixture 112 will contain water in an amount in a range having a lower limit of typically 10 weight percent, more typically 20 weight percent and even more typically 30 weight percent of the concentrated mixture 112 and having an upper limit of typically 80 weight percent, more typically 70 weight percent, even more typically 60 weight percent and most typically 50 weight percent. A particularly preferred range for the concentration of the precipitated protein for an intermediate storage application is from 50 weight percent to 70 weight percent of the concentrated mixture 112.

As will be appreciated from the above discussion, in most situations a majority of the liquid will be separated from the precipitated protein during the liquid separation 108 to prepare the concentrated mixture 112. Even in the situation when the concentrated mixture 112 is intended as a final formulation for administration, typically at least 50 weight percent of the liquid is removed during the liquid separation 108. More typically at least 75 weight percent and even more typically at least 90 weight percent of the liquid is removed during the liquid separation 108. In some situations, at least 95 weight percent or even 98 weight percent or more of the liquid is removed during the liquid separation 108. When extreme concentration of the protein precipitate is desired, centrifuging is one preferred liquid-solid separation technique.

Also as will be appreciated from the above discussion, the concentrated mixture 112 contains a much higher concentration of the precipitated protein than the concentration of the protein in the protein solution prepared during the solution preparation 102. Typically, the ratio of the concentration (on a weight basis) of the concentrated protein in the concentrated mixture 112 to the concentration of the protein dissolved in the original protein solution is at least 2, more typically at least 5 and even more typically at least 10. In some instances, the ratio can be at least 20, or even 40 or higher. For most applications when the concentrated mixture 112 is intended as a final formulation for administration, the ratio is typically at least 5 and more typically in a range of from 5 to 40. When the concentrated mixture 112 is designed for intermediate storage prior to further processing, the ratio is typically at least 25 and more typically at least 50, although in some situations the ratio can be at least 75 or even 100 or more.

A significant aspect of the present invention is that the concentrated mixture 112 is stable and can typically be stored for an appreciable time without substantial protein degradation. This is especially the case when a biocompatible polymer is used as the precipitating agent, and even more so when the biocompatible polymer is a preferred reverse-thermal gelation polymer. One aspect of this stability is that the concentrated mixture 112 contains very little protein in solution in the remaining liquid, because most or substantially all of the protein is usually precipitated out of solution during the protein precipitation 104. This is important and beneficial, because the precipitated protein is less susceptible to degradation and denaturation than protein remaining in solution. Proteins dissolved in aqueous media are highly susceptible to forming undesirable non-native aggregates. Because at least a significant quantity of the liquid medium is retained in the concentrated mixture 112, it is important to precipitate as much of the protein as possible during the protein precipitation 104, so that as little protein as possible remains in solution and susceptible to non-native aggregate formation. Typically no more than 5 weight percent, preferably no more than 2 weight percent, more preferably no more than 1 weight percent, even more preferably no more than 0.5 weight percent and most preferably no more than 0.2 weight percent of total protein in the concentrated mixture 112 is dissolved in the liquid medium retained in the concentrated mixture 112. Correspondingly, typically at least 95 weight percent, preferably at least 2 weight percent, more preferably at least 99 weight percent, even more preferably at least 99.5 weight percent and most preferably at least 99.8 weight percent of total protein in the concentrated mixture 112 is in the precipitated protein. Stability during storage is further enhanced by the presence of the biocompatible polymer that is retained in the concentrated mixture 112. The presence of the biocompatible polymer appears to provide some protection to the precipitated protein and its presence also prevents the precipitated protein from being redissolved in remaining liquid medium. Furthermore, the addition of a protein stabilizer during manufacture further aids stability of the concentrated mixture 112.

Figure 2:
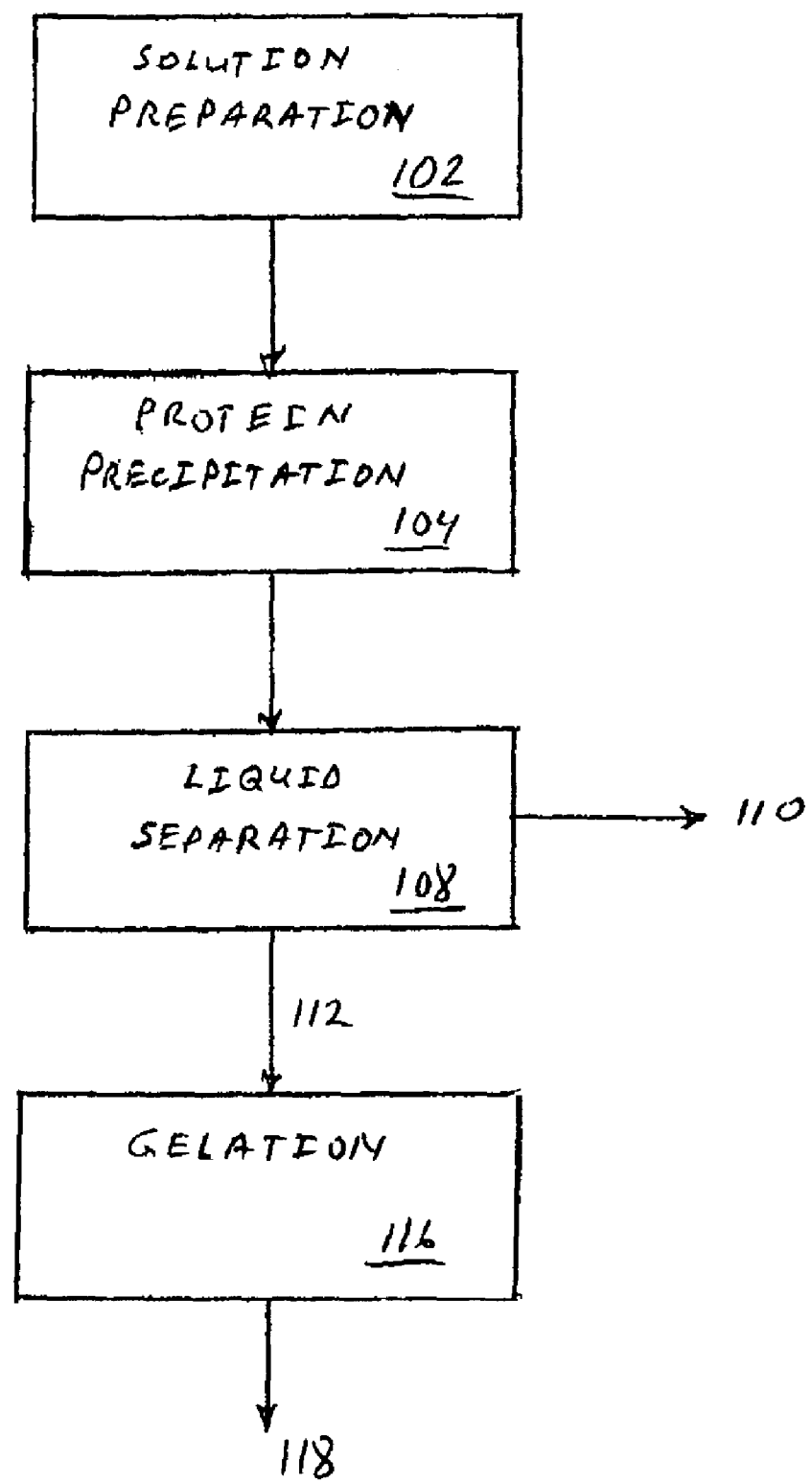
FIG. 2 is a generalized process block diagram showing one embodiment of the method of the present invention in which a concentrated mixture of precipitated protein is converted to a gel form for stability during storage.

An important aspect of the invention is that the concentrated mixture can be stored for an extended time without requiring expensive and cumbersome lyophilization. Storage of the concentrated mixture 112 typically involves standard refrigeration. In one embodiment, however, the concentrated mixture 112 includes a biocompatible reverse-thermal gelation polymer in a sufficient amount so that the polymer exists in a gel form at some temperature higher than the temperature at which the protein precipitation 104 is conducted, with the reverse-thermal liquid-gel transition temperature being typically no higher than 37° C., as discussed above. Referring now to FIG. 2, a generalized process block diagram is shown for the method of the invention in which the concentrated mixture 112 is subjected to gelation 116. During the gelation 116, the temperature of the concentrated mixture 112 is raised from a temperature below to a temperature above a reverse-thermal liquid-gel transition temperature, so that the polymer converts from a liquid form to a gel form. The resulting gel form 118 of the concentrated mixture 112 can then be stored. Following storage, the temperature of the gel form 118 of the concentrated mixture 112 could then be lowered below the reverse-thermal liquid-gel transition temperature to convert the polymer back to the liquid form for further processing or for administration. Storing the concentrated mixture 112 in the gel form reduces refrigeration costs and facilitates easy handling and shipment of the concentrated mixture 112.

Figure 3:
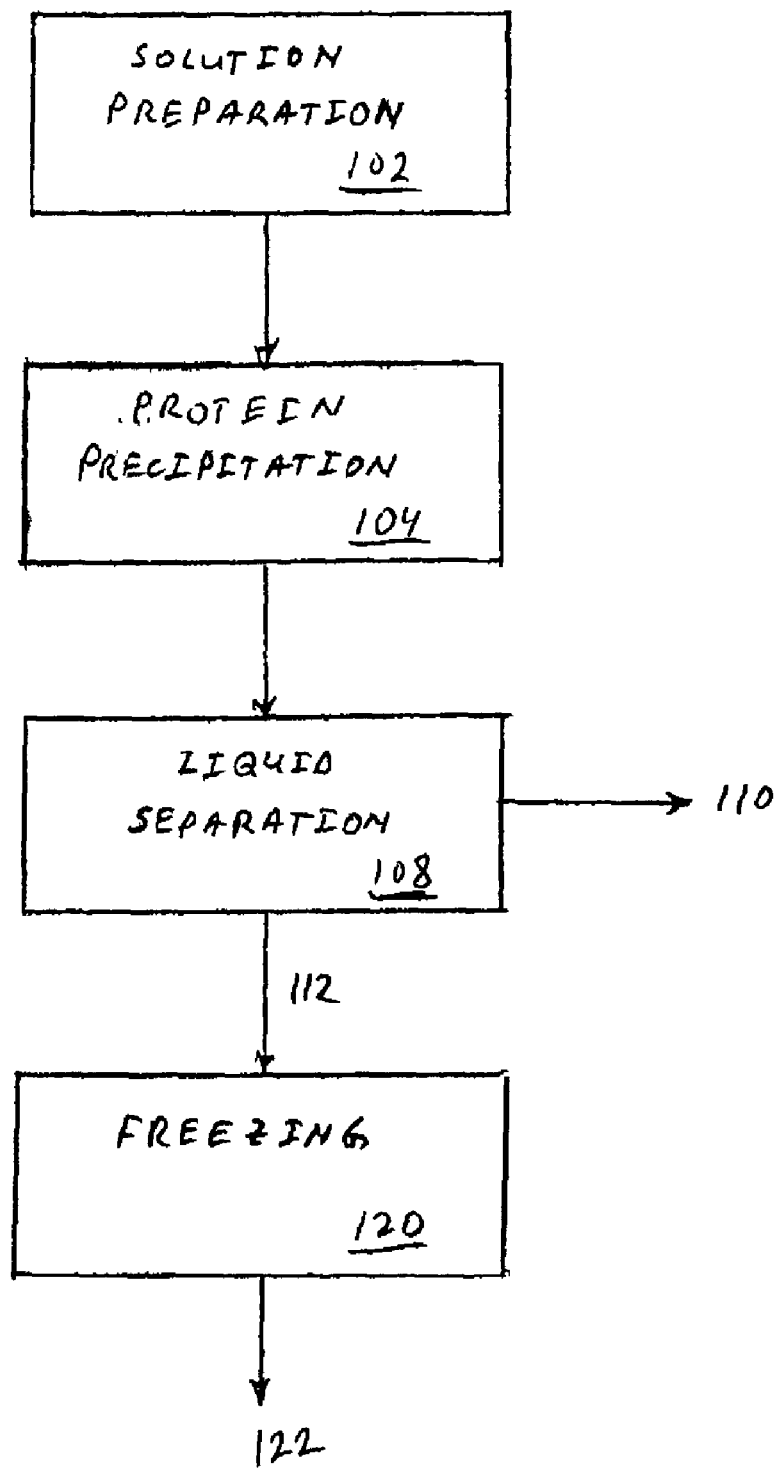
FIG. 3 is a generalized process block diagram showing one embodiment of the method of the present invention in which a concentrated mixture of precipitated protein is frozen for stability during storage.

In another embodiment, the concentrated mixture 112 can advantageously be frozen for long-term storage. This is a particularly useful embodiment for long-term storage that occurs at an intermediate point during manufacturing, such as when a batch of protein is to be held for an extended time between processing steps. Freezing is advantageous because the concentrated mixture 112 contains a substantially reduced volume of water that needs to be frozen, relative to freezing of a dilute solution or a more dilute suspension. Referring now to FIG. 3, a generalized process block diagram is shown for one embodiment of the method of the invention in which the concentrated mixture 112 is subjected to freezing 120. During the freezing 120, the temperature of the concentrated mixture 112 is lowered to below the freezing point of the liquid medium present in the concentrated mixture 112. Typically the temperature of the concentrated mixture 112 is lowered to a temperature in a range of from −20° C. to −80° C. The resulting frozen form 122 of the concentrated mixture 112 can then be stored for an extended time. Following storage, the liquid medium in the concentrated mixture 112 can then be melted to convert the concentrated mixture back to a more fluid form for further processing or for administration. It is important that with the present invention, freezing of the concentrated mixture 112 need not involve lyophilization, which would significantly add to processing expense and would make the precipitated protein harder to reconstitute in a more dilute formulation following storage.

A significant advantage with the present invention is the flexibility provided in relation to varying the concentration of the precipitated protein in the concentrated mixture 112, the ability to add a variety of additives during manufacture of the concentrated mixture 112, and the variety of storage and handling options available. Another advantage is that the concentrated mixture 112 can be further processed to impart additional characteristics for final pharmaceutical product as desired. For example, protein stabilizers and surfactants, if not added during solution preparation 102 or protein precipitation 104, could be added after the liquid separation 108 to change the characteristics of the concentrated mixture 112. One particularly important embodiment for further processing of the concentrated mixture is to add additional liquid medium to prepare a more dilute protein formulation. This may be advantageous, for example, to prepare a more dilute product with enhanced characteristics for administration after extended storage of the concentrated mixture 112.

Figure 4:
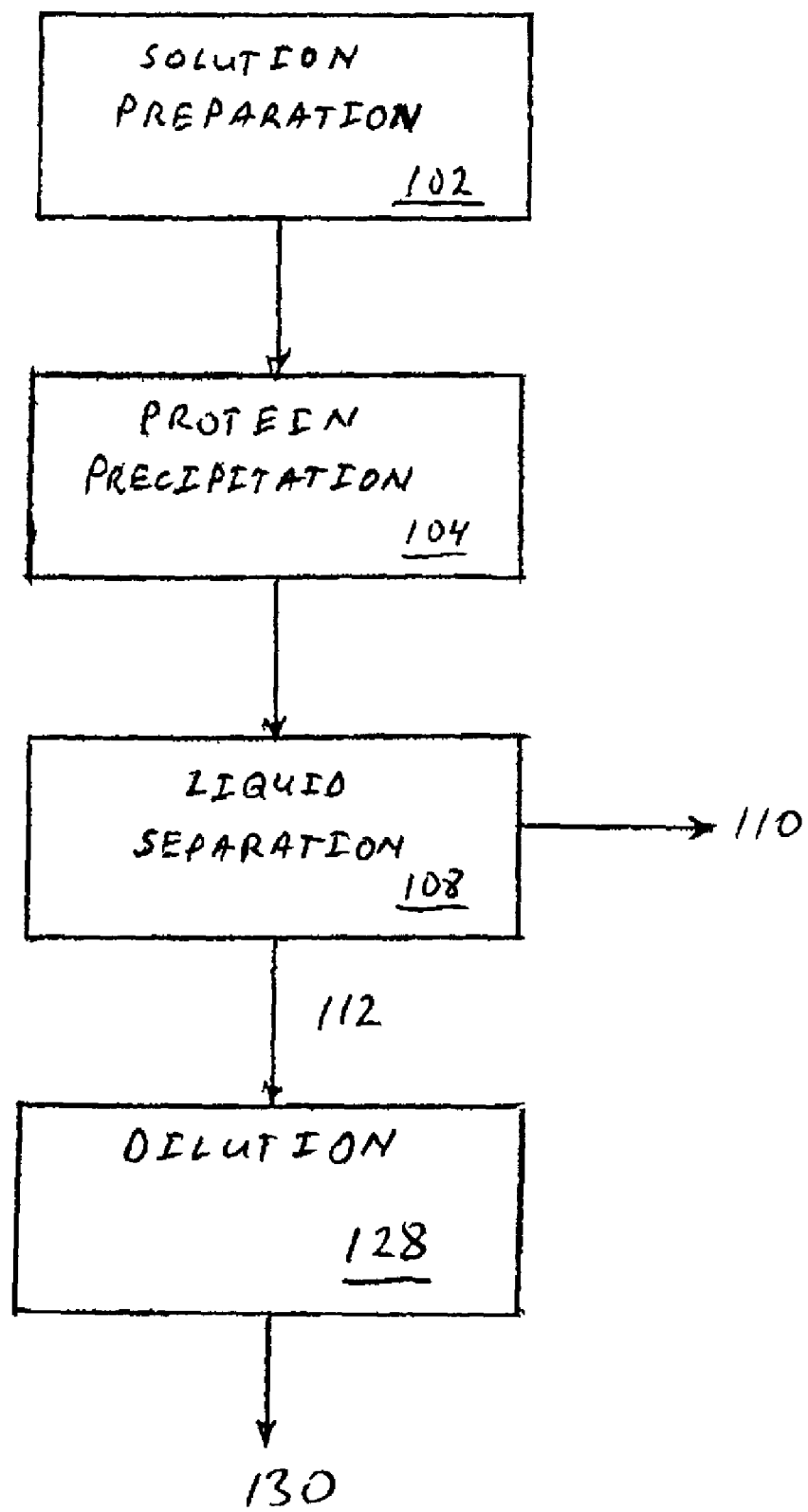
FIG. 4 is a generalized process block diagram showing one embodiment of the method of the present invention in which a concentrated mixture of precipitated protein is later diluted to prepare a more dilute mixture of the precipitated protein.

Referring now to FIG. 4, a generalized process block diagram is shown for one embodiment of the method of the present invention in which the concentrated mixture 112 is subjected to dilution 128 to prepare a dilute mixture 130. During the Dilution 128, diluting liquid medium is added to the concentrated mixture 112 so that the concentration of the precipitated protein in the dilute mixture 130 is reduced. The diluting liquid medium is typically an aqueous liquid that is compatible with aqueous liquid already present in the concentrated mixture 112. Although in some circumstances the addition of the diluting liquid medium will result in dissolution of some of the precipitated protein, the dissolution will be small enough that the concentration of dissolved protein in the dilute mixture 130 will be no more than 20 weight percent, and more often will be no more than 10 weight percent, of total protein in the dilute mixture 130, when the concentration of protein dissolved in the dilute mixture 130 has reached equilibrium following the dilution 128. Correspondingly, typically at least 80 weight percent, and more often at least 90 weight percent, of total protein in the dilute mixture 130 remains in the precipitated protein.

In most instances, it will be desirable that the diluting liquid medium be of such a character so as not to dissolve any substantial amount of the precipitated protein in the concentrated mixture 112 as a result of the dilution 128. Therefore, more typically no more than 5 weight percent, preferably no more than 2 weight percent, more preferably no more than 1 weight percent, even more preferably no more than 0.5 weight percent and most preferably no more than 0.2 weight percent of total protein in the concentrated mixture 112 is dissolved in the liquid medium of the dilute mixture 130, when the concentration of protein dissolved in the dilute mixture 130 has reached equilibrium following the dilution 128. Correspondingly, more typically at least 95 weight percent, preferably at least 98 weight percent, more preferably at least 99 weight percent, even more preferably at least 99.5 weight percent and most preferably at least 99.8 weight percent of total protein in the dilute mixture 130 remains in the precipitated protein.

To inhibit dissolution of protein as a result of the dilution 128, the diluting liquid medium can advantageously have dissolved therein some of the precipitating agent, or some other agent, having the effect of inhibiting, or even completely preventing, redissolution of precipitated protein. When used, the concentration of the precipitating agent in the diluting liquid medium, however, may often be smaller than the concentration of the precipitating agent in the liquid medium of the concentrated mixture 112, thereby reducing the concentration of the precipitating agent in the dilute mixture 130 relative to the concentrated mixture 112. This can be beneficial for reducing the viscosity of the formulation for improved injectability. In the case of a biocompatible polymer precipitating agent, the viscosity reduction can be due both to the presence of a larger proportion of liquid in the dilute mixture 130 and to a reduced concentration of the biocompatible polymer. In one embodiment, the diluting liquid medium is essentially free of the biocompatible polymer, to provide for a significant dilution of the concentration of the biocompatible polymer in the dilute mixture 130. However, in this situation, redissolution of the precipitated protein is likely depending upon the specific diluting medium used. To prevent any substantial redissolution of the precipitated protein, sufficient biocompatible polymer, or some other chemical agent effective to prevent the redissolution, should be present in the dilute mixture 130. Even when the diluting liquid medium is essentially free of the biocompatible polymer, the dilute mixture 130 will still include at least a small amount of the biocompatible polymer, and typically at least 0.1 weight percent of the biocompatible polymer.

A significant advantage of the concentrated mixture 112 is that it can be made so that the precipitated protein readily reconstitutes to prepare the dilute mixture 130. For ready reconstitution, the concentrated mixture 112 preferably includes at least 20 weight percent water and more preferably at least 30 weight percent water. The use of a biocompatible polymer precipitating agent is particularly preferred for preparing the concentrated mixture so that it readily reconstitutes to prepare the dilute mixture (or when it is desired to redissolve the precipitated protein). The concentration of water in the dilute mixture 130 will typically be at least 10 weight percentage points higher than the concentration of water in the concentrated mixture 112 (for example, increasing from 30 weight percent water in the concentrated mixture 112 to at least 40 weight percent water in the dilute mixture 130). Correspondingly, the concentration of the precipitated protein in the dilute mixture 130 will typically be at least 10 weight percentage points smaller than in the concentrated mixture 112 (for example, decreasing from 60 weight percent precipitated protein in the concentrated mixture to no more than 50 weight percent precipitated protein in the dilute mixture 130.) Often, the amount of diluting liquid medium added to the concentrated mixture 112 during the dilution 128 will be at least as large as, or even several times as large as, the liquid medium in the concentrated mixture 112. This could be the case, for example, when the concentrated mixture 112 is very highly concentrated in the precipitated protein (for example, from perhaps 40 weight percent to 70 weight percent precipitated protein in the concentrated mixture 112) for interim storage, with the dilution 128 being intended to dilute the formulation to a lower concentration of precipitated protein (for example, to a range of perhaps 10 weight percent to 30 weight percent precipitated protein in the dilute mixture 130) that has enhanced injectability or other properties desirable in a final pharmaceutical composition, such as for administration by IM, SC, IT or IA injection.

The ability to prepare the concentrated mixture 112 for extended storage of the protein in a stable form is particularly advantageous for storage that is often required between steps in manufacturing operations where protein compositions are made. For example, many therapeutic proteins are prepared in large quantities through fermentation processes. The produced proteins are then purified. The purification processes are typically operated at low protein concentration. During such processes, it is sometimes desirable to hold in-process materials at various stages of purification. With the present invention, the protein can be concentrated in the form of the concentrated mixture 112 for storage and then later subjected to the dilution 128 to reconstitute the protein in the diluted mixture 130 having a lower concentration of the precipitated protein. Moreover, rather than merely being diluted, the precipitated protein could be redissolved if desired for further processing, but this would typically not be the case. To redissolve the precipitated protein, sufficient aqueous media that is substantially free of the precipitating agent or other like agents would be added to accommodate complete solubility of the precipitated protein. In some situations, complete redissolution of the precipitated protein could be accompanied by multiple additions and separations of aqueous liquid to reduce the residual precipitating agent to a very low level, if desired.

Figure 5:
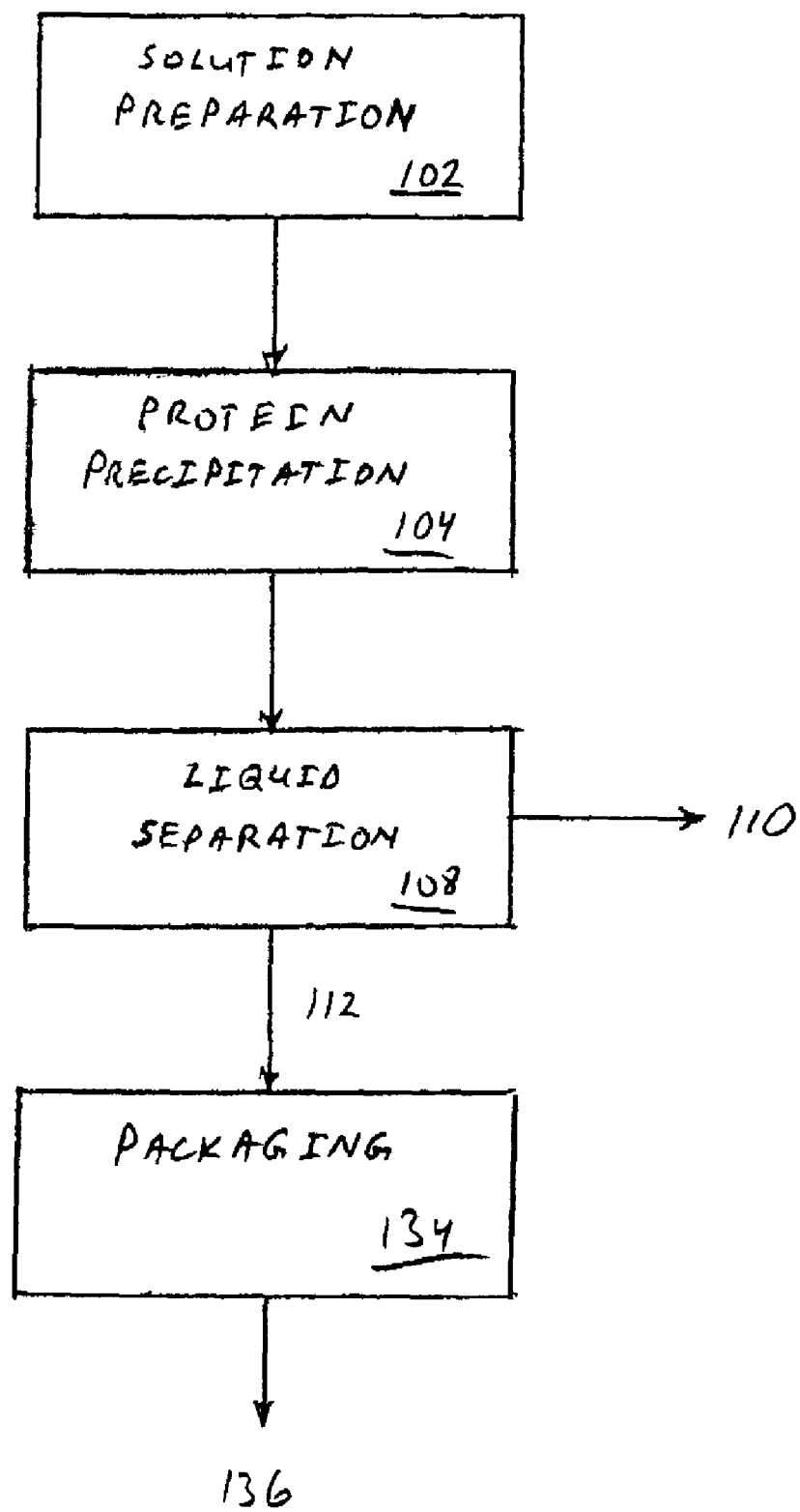
FIG. 5 is a generalized process block diagram showing one embodiment of the method of the present invention in which a concentrated mixture of precipitated protein is packaged.

In another aspect of the present invention, the precipitated protein mixture of the invention (e.g. the concentrated mixture 112 or the dilute mixture 130) could be packaged, such as in the form of vials or bottles containing a single dose of the precipitated protein for administration. Referring now to FIG. 5, a generalized process block diagram is shown for one embodiment of the method of the present invention in which the concentrated mixture 112 is packaged during a packaging 134 step to prepare a packaged pharmaceutical product 136. During the packaging 134, measured quantities of the concentrated mixture 112 are placed inside containers and the containers are sealed to prevent contamination during transportation and storage. In a preferred embodiment, the quantity of the concentrated mixture 112 sealed in each container is a single dose for administration of the precipitated protein. In an even more preferred embodiment, the volume of the concentrated mixture 112 containing the single dose is no larger than 1 mL, and is also preferably sufficiently injectable to permit administration by a technique such as IM, SC, IT or IA injection.

In another aspect, the present invention provides a pharmaceutical composition including a mixture of a precipitated protein and a liquid medium. The pharmaceutical composition is concentrated in the precipitated protein, but also includes a significant amount of liquid medium, typically an aqueous liquid, as discussed above. The pharmaceutical composition will also typically include at least some of the precipitating agent and may include other additives, such as for example a protein stabilizer and/or a surfactant. All of the discussion above concerning types and relative amounts of the various constituents apply equally here, and especially in relation to the properties of the concentrated mixture 112 and the dilute mixture discussed with reference to FIGS. 1-5. The pharmaceutical composition could be, for example, the concentrated mixture 112 or the dilute mixture 130 discussed with respect to FIGS. 1-5, or could be some other product including any of the constituents in any of the relative quantities and having any of the attributes as discussed above. The relative quantities of constituents in the pharmaceutical composition will depend upon the specific situation, for example upon the specific protein included in the composition and whether the composition is designed for interim storage or is a final formulation for administration, as discussed above.

As discussed above, it is beneficial for the pharmaceutical composition to include at least a significant amount of the liquid medium to facilitate ready reconstitution of the precipitated protein to prepare a more dilute formulation, if desired. It is, therefore, preferred that the precipitated protein in the pharmaceutical composition be maintained after precipitation in a formulation comprising typically at least 10 weight percent, preferably at least 20 weight percent and more preferably at least 30 weight percent water, although much higher water concentrations are often present, as discussed above with respect to FIGS. 1-5. Consistent with the above discussion in relation to FIGS. 1-5, the pharmaceutical composition will normally comprise at least 8 weight percent, preferably at least 10 weight percent and often an even higher concentration of the precipitated protein, and at least 0.1 weight percent, preferably at lest 5 weight percent and often an even higher concentration of the biocompatible polymer. Protein stabilizers, when used, will ordinarily be present at a concentration of from 10 weight percent to 1000 weight percent relative to precipitated protein. Surfactants, when used, will ordinarily be present at a concentration of from 0.001 weight percent to 1 weight percent relative to the precipitated protein. When a quantity of an additive is specified herein as being at a weight percent relative to the precipitated protein, it is meant that the quantity of the additive is determined as a weight that is that relative percentage of the weight of the precipitated protein.

In one embodiment, the pharmaceutical composition is in a sealed container, as discussed above, and preferably the quantity of the pharmaceutical composition contained in the sealed container has a total volume of no larger than 1 mL. The quantity of the pharmaceutical composition contained in the sealed container also preferably includes a single dose of the precipitated protein for administration.

In one embodiment, the pharmaceutical composition is in a sufficiently injectable form to be administrable by injection. In a preferred embodiment, the pharmaceutical composition is administrable by IM, SC, IT or IA injection, and more preferably through no larger than an 18 gauge hypodermic needle. When administered by injection, the pharmaceutical composition will be contained in an injection device, such as for example a syringe, and preferably a syringe having no larger than an 18 gauge hypodermic needle.

In another aspect the present invention provides a method for using the pharmaceutical composition to administer a precipitated protein to a patient. The administration is preferably by injection, as discussed above. Preferably a single injected dose of the precipitated protein is contained in a volume of the pharmaceutical composition that is no larger than 1 mL. In one preferred embodiment, the pharmaceutical composition includes a surfactant that enhances injectability of the pharmaceutical composition.

In another aspect the present invention provides a method for using the pharmaceutical composition for extended storage of a precipitated protein. In a preferred embodiment, the pharmaceutical composition will include at least a protein stabilizer for extended storage applications.

EXAMPLES

Additional objects, advantages, and novel features of this invention will become apparent to those skilled in the art upon examination of the following examples thereof, which are intended to further describe and aid in the understanding of the invention and not to limit the scope of the invention in any way.

Example 1

A 20 mL homogeneous 10 mg/mL solution of bovine immunoglobulin (B-IgG) (CalBiochem, cat #345876) is prepared in normal saline and chilled to 2-8° C. by dissolution of the dry B-IgG into 150 mM NaCl, 0.1% $NaN_3$. Stock solution of 30% (wt:vol) Pluronic™ F127 (BASF) in deionized water is prepared by dissolving the polymer into refrigerated 2-8° C. water with periodic mixing until a homogenous solution is formed. A volume of 20 mL of the Pluronic™ stock solution is placed in a glass container equipped with a magnetic stir bar and maintained at 2-8° C. while being stirred. To this stirred Pluronic™ solution is slowly added the B-IgG solution. The resulting mixture immediately forms a precipitate. The mixture is stirred at 2-8° C. for 30 minutes. The resulting suspension is centrifuged at 1300 rmp for 15 minutes. Approximately 39 mL of supernatant is decanted and analyzed for protein content. The resulting pellet (concentrate mixture) is a dense, but pliable material.

Example 2

Solutions of B-IgG and Pluronic™ F127 are prepared as described in Example 1. 500 µL of the B-IgG solution is added to 500 µL of the F127 solution. The resulting mixture is agitated by end-over-end inversion at 2-8° C. for 30 minutes. The precipitate is separated by centrifugation and decanting the supernatant fluid. The remaining pellet (concentrated mixture) is then re-dissolved by the addition of 1 mL of normal saline. The saline/pellet mixture is incubated at 2-8° C. for approximately 16 hours after which time brief vortexing results in a clear, colorless solution.

Example 3

Solutions of bovine immunoglobulin and Pluronic™ F127 are prepared as described above in Example 1, with the exception that 10% (wt:vol) mannitol is included in the B-IgG solution. The solutions are then mixed by the addition of the B-IgG solution to the Pluronic™ solution. The resulting mixture is agitated by end-over-end inversion at 2-8° C. for 30 minutes. The precipitate is separated by centrifugation and the separated precipitate (concentrated mixture) is found to be fluid and viscous. The separated precipitate (concentrate mixture) is sufficiently injectable to be placed into a 1 cc plastic syringe and easily dispensed through a 22 gauge hypodermic needle.

Example 4

Example 3 is repeated except adding 0.005% Tween™ rather than 10% mannitol. The resulting pellet (concentrated mixture) is also soft and can be pushed through a 27 gauge hypodermic needle.

Example 5

Example 3 is repeated except that either 10% Trehalose, 10% Dextrose, 10% Fructose, or 1% PEG 600 (polyethylene glycol) is added rather than the mannitol. Resulting pellets (concentrated mixtures) are hard and could not be pushed through an 18 gauge hypodermic needle.

Example 6

A 15 mg/mL solution of polyclonal Rabbit-anti-Ovalbumin is prepared by reconstitution of a lyophilized cake with 5 mL of normal saline (Cappel, Cat #55304). The resulting solution is cooled to 2-8° C. A 30% (wt:vol) solution of Pluronic™ F127 is prepared as described in Example 1. 250 µL of the antibody solution is then added to 250 µL of the polymer solution. The resulting mixture is then agitated by end-over-end inversion at 2-8° C. for 30 minutes. The precipitate is separated by centrifugation and decanting the supernatant fluid. The resulting pellet (concentrated mixture) is re-dissolved in normal saline as described in Example 2. Analysis of the degree of nonspecific oligomerization and reactive affinity of the re-dissolved antibody is performed by size exclusion chromatography and ELISA respectively. No change is detected in either analysis of the starting versus re-dissolved protein material.

Example 7

Example 6 is repeated with the exception that the resulting pellet (concentrated mixture) is held for 2 months at 2-8° C. without measurable change in either nonspecific oligomerization and/or reactive affinity, indicating that the protein in the concentrated mixture is stable for an extended time.

Example 8

Example 7 is repeated, except that to the Rabbit-anti-Ovalbumin solution is added 0.005% Tween™, and resulting concentrated mixture is held for 2 months at 2-8° C. without measurable change in either nonspecific oligomerization and/or reactive affinity, indicating that the protein in the concentrated mixture is stable for an extended time.

Example 9

Example 7 is repeated, except that to the Rabbit-anti-Ovalbumin solution is added 10% (wt:vol) mannitol, and resulting concentrated mixture is held for 2 months at 2-8° C. without measurable change in either nonspecific oligomerization and/or reactive affinity, indicating that the protein in the concentrated mixture is stable for an extended time.

Example 10

Example 6 is repeated, except that to the Rabbit-anti-Ovalbumin solution is added 0.005% Tween™, and resulting concentrated mixture is subjected to a freeze/thaw cycle with the concentrated mixture held in a frozen state for 2 weeks at a temperature of either −20° C. or −80° C. No measurable change in either nonspecific oligomerization and/or reactive affinity is detected, indicating that the protein in the concentrated mixture is stable through the freeze/thaw cycles.

Example 11

Example 6 is repeated, except that the resulting concentrated mixture is covered with 250 µL of an aqueous solution containing 30%, 22.5% or 15% (wt:vol) Pluronic™ F127. The temperature of each sample is raised to 40° C. and held for 3 weeks. Each sample shows some increase in oligomerization, but no difference in the reactive affinity of the protein, indicating that the some protein degradation has occurred.

Example 12

Example 6 is repeated, except that either 10 mM or 100 mM zinc chloride is added to the Rabbit-anti-Ovalbumin solution. The precipitated protein in the concentrated mixture is not readily redissolvable in normal saline.

The foregoing discussion of the invention has been presented for purposes of illustration and description. The foregoing is not intended to limit the invention to only the form or forms specifically disclosed herein. Although the description of the invention has included description of one or more embodiments and certain variations and modifications, other variations and modifications are within the scope of the invention, e.g., as may be within the skill and knowledge of those in the art after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter. Furthermore, any feature described with respect to any disclosed embodiment may be combined in any combination with one or more features of any other embodiment or embodiments. For example, additional processing steps can be included at any point during or after processing disclosed in any of the process embodiments of FIGS. 1-5, so long as the additional steps are not incompatible with the disclosed processing. Moreover, processing steps disclosed in any of FIGS. 1-5 can be combined with any other processing steps disclosed in FIGS. 1-5.

What is claimed is:

1. A pharmaceutical product, comprising a pharmaceutical composition contained within a sealed container, wherein:
   the pharmaceutical composition comprises:
   (i) polyoxyalkylene block copolymer;
   (ii) at least 10 weight percent, relative to weight of the pharmaceutical composition, of a precipitated protein, the precipitated protein being in the form of a precipitate having been prepared by precipitation from an aqueous liquid solution with the polyoxyalkylene block copolymer; and
   (iii) at least 10 weight percent, relative to the weight of the pharmaceutical composition, water.

2. A pharmaceutical product, comprising a pharmaceutical composition contained within a sealed container, wherein:
   the pharmaceutical composition comprises:
   (i) biocompatible polymer precipitating agent;
   (ii) at least 10 weight percent of a precipitated protein, the precipitated protein being in the form of a precipitate having been prepared by precipitation from an aqueous liquid solution with the biocompatible polymer precipitating agent; and
   (iii) at least 10 weight percent water;
   wherein the pharmaceutical composition has a total volume of no larger than 1 mL.

3. A method for administering a protein, comprising injecting into a patient a pharmaceutical composition, the pharmaceutical composition comprising:
   (i) polyoxyalkylene block copolymer;
   (ii) at least 10 weight percent, relative to weight of the pharmaceutical composition, precipitated protein, the precipitated protein being in the form of a precipitate having been prepared by precipitation from an aqueous liquid solution with the polyoxyalkylene block copolymer; and
   (iii) at least 10 weight percent, relative to the weight of the pharmaceutical composition, water.

4. The pharmaceutical product of claim 1, wherein the pharmaceutical composition comprises at least 20 weight percent, relative to weight of the pharmaceutical composition, of the water; and
   wherein the precipitated protein has been maintained since the precipitation in a formulation comprising no less than 20 weight percent water.

5. The pharmaceutical product of claim 1, wherein the water is frozen.

6. The pharmaceutical product of claim 1, wherein the pharmaceutical composition comprises from 10 to 50 weight percent, relative to the weight of the pharmaceutical composition, of the precipitated protein and from 50 to 90 weight percent, relative to the weight of the pharmaceutical composition, of the water.

7. The pharmaceutical product of claim 1, wherein the pharmaceutical composition comprises at least 0.1 weight percent, relative to the weight of the pharmaceutical composition, of the polyoxyalkylene block copolymer.

8. The pharmaceutical product of claim 1, wherein the concentration of the polyoxyalkylene block copolymer in the pharmaceutical composition is smaller than the concentration of the polyoxyalkylene block copolymer during the precipitation.

9. The pharmaceutical product of claim 1, wherein the pharmaceutical composition comprises at least 10 weight percent, relative to the weight of the pharmaceutical composition, of the polyoxyalkylene block copolymer.

10. The pharmaceutical product of claim 1, wherein the pharmaceutical composition comprises from 10 weight percent to 30 weight percent, relative to the weight of the pharmaceutical composition, of the polyoxyalkylene block copolymer.

11. The pharmaceutical product of claim 1, wherein the precipitated protein comprises at least 95 weight percent of total protein in the pharmaceutical composition.

12. The pharmaceutical product of claim 1, wherein the precipitated protein comprises at least 99 weight percent of total protein in the pharmaceutical composition.

13. The pharmaceutical product of claim 12, wherein the pharmaceutical composition comprises at least 5 weight percent, relative to the weight of the pharmaceutical composition, of the polyoxyalkylene block copolymer.

14. The pharmaceutical product of claim 13, wherein the polyoxyalkylene block copolymer is Poloxamer 407 and the protein is an antibody.

15. The pharmaceutical product of claim 1, wherein the polyoxyalkylene block copolymer is a reverse-thermal gelation polymer.

16. The pharmaceutical product of claim 15, wherein the pharmaceutical composition comprises at least some of the polyoxyalkylene block copolymer and the concentration of the polyoxyalkylene block copolymer in the pharmaceutical composition is not large enough for the pharmaceutical composition to exhibit reverse-thermal gelation.

17. The pharmaceutical product of claim 1, wherein the polyoxyalkylene block copolymer is Poloxamer 407 and the protein is an antibody.

18. The pharmaceutical product of claim 1, wherein the protein is a macromolecular protein.

19. The pharmaceutical product of claim 1, wherein the protein is an antibody.

20. The pharmaceutical product of claim 1, wherein the pharmaceutical composition comprises a protein-stabilizer.

21. The pharmaceutical product of claim 1, wherein the pharmaceutical composition comprises a surfactant.

22. A pharmaceutical product, comprising a pharmaceutical composition in an injectable form contained in an injection device, wherein:
the pharmaceutical composition comprises:
(i) polyoxyalkylene block copolymer;
(ii) at least 10 weight percent, relative to weight of the pharmaceutical composition, precipitated protein, the precipitated protein being in the form of a precipitate having been prepared by precipitation from an aqueous liquid solution with the polyoxyalkylene block copolymer; and
(iii) at least 10 weight percent, relative to the weight of the pharmaceutical composition, water.

23. The pharmaceutical product of claim 22, wherein the injection device comprises a syringe.

24. The pharmaceutical product of claim 23, wherein the syringe has a hypodermic needle with no larger than an 18 gauge opening.

25. The pharmaceutical product of claim 1, wherein the sealed container comprises an injection device in which the pharmaceutical composition is disposed.

26. The pharmaceutical product of claim 1, wherein no more than 5 weight percent of total protein in the pharmaceutical composition is in solution.

27. The pharmaceutical product of claim 26, wherein:
the pharmaceutical composition comprises from 10 weight percent to 35 weight percent, relative to the weight of the pharmaceutical composition, of the precipitated protein, at least 10 weight percent, relative to the weight of the pharmaceutical composition, of the polyoxyalkylene block copolymer and at least 20 weight percent of the water, relative to the weight of the pharmaceutical composition.

28. The pharmaceutical product of claim 27, wherein the pharmaceutical composition comprises a concentration of surfactant of from 0.001 weight percent to 1 weight percent relative to weight of the precipitated protein, the surfactant being different than the polyoxyalkylene block copolymer.

29. The pharmaceutical product of claim 28, wherein the pharmaceutical composition comprises a concentration of protein stabilizer in a range of from 10 weight percent to 1000 weight percent relative to the weight of the precipitated protein, the protein-stabilizer being different than the polyoxyalkylene block copolymer.

30. The pharmaceutical product of claim 27, wherein the polyoxyalkylene block copolymer is of a formula $$HO(C_2H_4O)_b(C_3H_6O)_a(C_2H_4O)_bH$$

where a is an integer in a range of from 15 to 80, and each b is an integer in a range of from 50 to 150.

31. The pharmaceutical product of claim 22, wherein the pharmaceutical composition comprises at least 30 weight percent, relative to the weight of the pharmaceutical composition, of the water.

32. The pharmaceutical product of claim 31, wherein the pharmaceutical composition comprises at least 5 weight percent, relative to the weight of the pharmaceutical composition, of the polyoxyalkylene block copolymer.

33. The pharmaceutical product of claim 32, wherein no more than 5 weight percent of total protein in the pharmaceutical composition is in solution.

34. The pharmaceutical product of claim 22, wherein the polyoxyalkylene block copolymer is Poloxamer 407 and the protein is an antibody.

35. The pharmaceutical product of claim 33, wherein the pharmaceutical composition comprises from 10 weight percent to 35 weight percent, relative to the weight of the pharmaceutical composition, of the precipitated protein.

36. The pharmaceutical product of claim 35, wherein the pharmaceutical composition comprises at least 20 weight percent, relative to the weight of the pharmaceutical composition, of the precipitated protein.

37. The pharmaceutical product of claim 36, wherein the pharmaceutical composition comprises a surfactant, the surfactant being different than the polyoxyalkylene block copolymer.

38. The pharmaceutical product of claim 36, wherein the pharmaceutical composition comprises a protein-stabilizer, the protein-stabilizer being different than the polyoxyalkylene block copolymer.

39. The pharmaceutical product of claim 36, wherein the polyoxyalkylene block copolymer is a reverse-thermal gelation polymer and is present at a concentration at which the pharmaceutical composition does not exhibit reverse-thermal gelation.

40. The pharmaceutical product of claim 36, wherein the precipitated protein is an antibody.

41. The method of claim 3, wherein the pharmaceutical composition comprises at least 30 weight percent, relative to the weight of the pharmaceutical composition, of the water.

42. The method of claim 41, wherein the pharmaceutical composition comprises at least 5 weight percent, relative to the weight of the pharmaceutical composition, of the polyoxyalkylene block copolymer.

43. The method of claim 42, wherein no more than 5 weight percent of total protein in the pharmaceutical composition is in solution.

44. The method of claim 43, wherein the polyoxyalkylene block copolymer is Poloxamer 407 and the protein is an antibody.

45. The method of claim 43, wherein the pharmaceutical composition comprises from 10 weight percent to 35 weight percent, relative to the weight of the pharmaceutical composition, of the precipitated protein.

46. The method of claim 45, wherein the pharmaceutical composition comprises at least 20 weight percent, relative to the weight of the pharmaceutical composition, of the precipitated protein.

47. The method of claim 46, wherein the pharmaceutical composition comprises a surfactant, the surfactant being different than the polyoxyalkylene block copolymer.

48. The method of claim 46, wherein the pharmaceutical composition comprises a protein-stabilizer, the protein-stabilizer being different than the polyoxyalkylene block copolymer.

49. The method of claim 46, wherein the polyoxyalkylene block copolymer is a reverse-thermal gelation polymer and is present at a concentration at which the pharmaceutical composition does not exhibit reverse-thermal gelation.

50. The method of claim 46, wherein the precipitated protein is an antibody.

51. The pharmaceutical product of claim 26, wherein the protein is an antibody.

52. The pharmaceutical product of claim 51, wherein the polyoxyalkylene block copolymer is Poloxamer 407.

53. The pharmaceutical product of claim 51, wherein the polyoxyalkylene block copolymer is a polyoxyethylene-polyoxypropylene block copolymer.

54. The pharmaceutical product of claim 30, wherein the protein is an antibody.

55. The pharmaceutical product of claim 40, wherein the polyoxyalkylene block copolymer is Poloxamer 407.

56. The method of claim 50, wherein the polyoxyalkylene block copolymer is Poloxamer 407.

* * * * *